(12) United States Patent
Li et al.

(10) Patent No.: US 9,669,247 B2
(45) Date of Patent: Jun. 6, 2017

(54) THIFENSULFURON HYDROLASE GENE TSME AND USES THEREOF

(75) Inventors: Shunpeng Li, Jiangsu (CN); Jian He, Jiangsu (CN); Baojian Hang, Jiangsu (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 580 days.

(21) Appl. No.: 14/234,824

(22) PCT Filed: Jul. 17, 2012

(86) PCT No.: PCT/CN2012/078765
§ 371 (c)(1),
(2), (4) Date: Jan. 24, 2014

(87) PCT Pub. No.: WO2013/013585
PCT Pub. Date: Jan. 31, 2013

(65) Prior Publication Data
US 2014/0325700 A1    Oct. 30, 2014

(30) Foreign Application Priority Data

Jul. 25, 2011 (CN) .......................... 2011 1 0207944

(51) Int. Cl.
| | | |
|---|---|---|
| *C12N 9/14* | (2006.01) | |
| *C12N 9/18* | (2006.01) | |
| *A62D 3/02* | (2007.01) | |
| *C02F 101/32* | (2006.01) | |
| *C12N 15/82* | (2006.01) | |
| *C02F 3/34* | (2006.01) | |
| *A62D 101/04* | (2007.01) | |
| *A62D 101/28* | (2007.01) | |
| *A62D 101/26* | (2007.01) | |
| *C02F 101/36* | (2006.01) | |

(52) U.S. Cl.
CPC ................ *A62D 3/02* (2013.01); *C02F 3/342* (2013.01); *C12N 9/14* (2013.01); *C12N 9/18* (2013.01); *C12N 15/8259* (2013.01); *C12N 15/8274* (2013.01); *C12N 15/8278* (2013.01); *A62D 2101/04* (2013.01); *A62D 2101/26* (2013.01); *A62D 2101/28* (2013.01); *C02F 2101/36* (2013.01); *C02F 2101/40* (2013.01)

(58) Field of Classification Search
CPC ... A01H 5/10; A01H 1/00; A62D 3/02; C12N 15/8274
See application file for complete search history.

(56) References Cited

PUBLICATIONS

Hang et al, 2012, Applied and Environmental Microbiology 78(6):1962-1968.*
Huang et al, International Biodeterioration & Biodegradation 60 (2007) 152-158.*
Genbank Accession JN617866, first available online Jan. 2, 2012.*
Chen, Yin, et al. "Complete genome sequence of the aerobic facultative methanotroph Methylocella silvestris BL2." Journal of bacteriology 192.14 (2010): 3840-3841.*
Brown, Hugh M., et al. "Degradation of thifensulfuron methyl in soil: role of microbial carboxyesterase activity." Journal of agricultural and food chemistry 45.3 (1997): 955-961.*

* cited by examiner

Primary Examiner — Lee A Visone
Assistant Examiner — Fan Fan
(74) Attorney, Agent, or Firm — Zareefa B. Flener; Flener IP Law, LLC (57) ABSTRACT

The present invention relates to the field of applied and environmental microorganism and agriculture. Disclosed are a thifensulfuron hydrolase gene tsmE and uses thereof. The thifensulfuron hydrolase gene tsmE has a nucleotide sequence of SEQ ID NO. 1, full length of 1194 bp, and G+C content of 51.09%, and encodes 398 amino acids with an amino acid sequence of SEQ ID NO. 2. The thifensulfuron hydrolase TsmE provided by the present invention can degrade completely 100 mg/L thifensulfuron within 1 hour into the herbicidally inactive product thiophenesulfonic acid; in addition, the TsmE also degrade completely 100 mg/L haloxyfop-R-methyl within 1 hour. Therefore, the thifensulfuron hydrolase gene tsmE is useful in construction of thifensulfuron-resistant transgenic crops and bioremediation of thifensulfuron or haloxyfop-R-methyl-contaminated environments.

7 Claims, 8 Drawing Sheets

SEQUENCE LISTING

<160> NUMBER OF SEQ ID NOS: 4

<210> SEQ ID NO 1
<211> LENGTH: 1194
<212> TYPE: DNA
<213> ORGANISM: Methylophilus sp. S113
<220> FEATURE:
<223> OTHER INFORMATION: Thiefensulfuron Hydrolase TSME

<400> SEQUENCE: 1

| | | | | | |
|---|---|---|---|---|---|
| atggaaaccg | ataaaaaaac | cggaacgtcc | cgcagatcat | ttgtgaaggc | tgctggaacc | 60 |
| ggcgcaatag | gaatagcgac | gctgccgctt | tcgactgcaa | ctgctttcgc | ggaaactgac | 120 |
| aacgtggagc | ttgcccaatc | gaagcggaag | gttgtccttg | ctgaacaagg | cagtttctac | 180 |
| atcggggca | gaacagtaac | cgggcctgga | aaattcgatc | cgtcaaagcc | ggtaattcca | 240 |
| tattccaacg | aaggtgccac | gttttatatc | aatcaaatgt | acgtaaactt | tcaagctcct | 300 |
| gtgcgccctc | gtgggctgcc | tctagtcttt | tggcatgggg | gcggactaac | cggccatatc | 360 |
| tgggaatcta | ccccagacgg | ccgccccgga | tttcagaccc | tctttgttca | agatcggcat | 420 |
| acggtctaca | cgattgatca | gccagggcgc | ggaaggggca | atattcctac | ctttaatggc | 480 |
| ccttttgggc | agttggaaga | gagtcgatt | gttaacactg | ttaccggaaa | ctccagtaaa | 540 |
| gaaggagcgt | gggttagaga | tcgactaggg | cccgctcccg | gccagttttt | tgagaacagc | 600 |
| caattcccac | gtggttatga | agacaactac | ttcaaggaga | tggggttcag | tccgtcgatc | 660 |
| tcatcagatg | agatagtcga | cgctgttgtt | aaactagtaa | ctcacatagg | tccttgtgtt | 720 |
| ctggtgaccc | attcggcttc | cggagtactg | ggcatgcgag | tcgcgacaca | cgccaagaac | 780 |
| gtgaggggga | tcgttgctta | tgagcctgcg | acaagtatct | ttcccaaagg | aaaagtgcct | 840 |
| gagataccgc | ctctcgccga | taaaaagtcg | caaattttcc | cgccgttcga | gatccaggag | 900 |
| tcttacttta | gaagctcgc | gaagataccc | attcagtttg | tcttcggaga | taatatcccc | 960 |
| aagaaccta | atccgccta | ttggttcttg | gactggtgga | gagtcactcg | ctacgctcac | 1020 |
| agcttgtcac | tcgaggctat | caataagctc | ggtggtcaag | cgtctctttt | ggatttgccg | 1080 |
| actgcgggac | ttcgcggcaa | cacgcatttt | ccattcaccg | accggaataa | cgtgcaggtc | 1140 |
| gcttctctgt | tatctgattt | cctcggaaag | cacggcttag | atcagaacga | aagc | 1194 |

<210> SEQ ID NO 2
<211> LENGTH: 398
<212> TYPE: PRT
<213> ORGANISM: Methylophilus sp. S113
<220> FEATURE:
<223> OTHER INFORMATION: Thiefensulfuron Hydrolase TSME

<400> SEQUENCE: 2

Met Glu Thr Asp Lys Lys Thr Gly Thr Ser Arg Arg Ser Phe Val
1               5                   10                  15

Lys Ala Ala Gly Thr Gly Ala Ile Gly Ile Ala Thr Leu Pro Leu
                20                  25                  30

Ser Thr Ala Thr Ala Phe Ala Glu Thr Asp Asn Val Glu Leu Ala
                35                  40                  45

Gln Ser Lys Arg Lys Val Val Leu Ala Glu Gln Gly Ser Phe Tyr
                50                  55                  60

Ile Gly Gly Arg Thr Val Thr Gly Pro Gly Lys Phe Asp Pro Ser
                65                  70                  75

Lys Pro Val Ile Pro Tyr Ser Asn Glu Gly Ala Thr Phe Tyr Ile
                80                  85                  90

```
Asn Gln Met Tyr Val Asn Phe Gln Ala Pro Val Arg Pro Arg Gly
                 95                 100                 105

Leu Pro Leu Val Phe Trp His Gly Gly Leu Thr Gly His Ile
            110                 115                 120

Trp Glu Ser Thr Pro Asp Gly Arg Pro Gly Phe Gln Thr Leu Phe
            125                 130                 135

Val Gln Asp Arg His Thr Val Tyr Thr Ile Asp Gln Pro Gly Arg
            140                 145                 150

Gly Arg Gly Asn Ile Pro Thr Phe Asn Gly Pro Phe Gly Gln Leu
            155                 160                 165

Glu Glu Glu Ser Ile Val Asn Thr Val Thr Gly Asn Ser Ser Lys
            170                 175                 180

Glu Gly Ala Trp Val Arg Asp Arg Leu Gly Pro Ala Pro Gly Gln
            185                 190                 195

Phe Phe Glu Asn Ser Gln Phe Pro Arg Gly Tyr Glu Asp Asn Tyr
            200                 205                 210

Phe Lys Glu Met Gly Phe Ser Pro Ser Ile Ser Ser Asp Glu Ile
            215                 220                 225

Val Asp Ala Val Val Lys Leu Val Thr His Ile Gly Pro Cys Val
            230                 235                 240

Leu Val Thr His Ser Ala Ser Gly Val Leu Gly Met Arg Val Ala
            245                 250                 255

Thr His Ala Lys Asn Val Arg Gly Ile Val Ala Tyr Glu Pro Ala
            260                 265                 270

Thr Ser Ile Phe Pro Lys Gly Lys Val Pro Glu Ile Pro Pro Leu
            275                 280                 285

Ala Asp Lys Lys Ser Gln Ile Phe Pro Pro Phe Glu Ile Gln Glu
            290                 295                 300

Ser Tyr Phe Lys Lys Leu Ala Lys Ile Pro Ile Gln Phe Val Phe
            305                 310                 315

Gly Asp Asn Ile Pro Lys Asn Pro Lys Ser Ala Tyr Trp Phe Leu
            320                 325                 330

Asp Trp Trp Arg Val Thr Arg Tyr Ala His Ser Leu Ser Leu Glu
            335                 340                 345

Ala Ile Asn Lys Leu Gly Gly Gln Ala Ser Leu Leu Asp Leu Pro
            350                 355                 360

Thr Ala Gly Leu Arg Gly Asn Thr His Phe Pro Phe Thr Asp Arg
            365                 370                 375

Asn Asn Val Gln Val Ala Ser Leu Leu Ser Asp Phe Leu Gly Lys
            380                 385                 390

His Gly Leu Asp Gln Asn Glu Ser
            395

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
tgcagacata tggaaaccga taaaaaaac                                29

<210> SEQ ID NO 4
<211> LENGTH: 32
```

```
<212> TYPE: DNA
<213> ORGANISM: Artificial Sequence
<220> FEATURE:
<223> OTHER INFORMATION: Primer

<400> SEQUENCE: 4
tgcagagaat tcccttccat aagagcgccg at                                    32
```

THIFENSULFURON HYDROLASE GENE TSME AND USES THEREOF

FIELD OF INVENTION

The present invention relates to the field of applied and environmental microorganism and agriculture, and to a thifensulfuron hydrolase gene tsmE and uses thereof.

RELATED ART

Application of herbicide allows alleviation of strength of farm labor and ensures regular production of agriculture, whereas its residues also bring about serious problems of crop damage by chemicals. It was statistically estimated that, in China, the farmland was damaged by herbicide with area up to 30 million acres per annum, wherein the serious damage by chemicals covered 5 million acres, causing economical loss of billions of RMB¥ per annum, and herbicide-resistant transgene represents an optimal option to prevent crops from herbicide injury. With the rapid development in study and application, the sulfonylurea herbicides have already been the main herbicides at the third position next to organophosphorus and acetamide herbicides, with the annual global sales up to over 3 billion dollars. The sulfonylurea herbicides applied in the country covered over 2 million hectares and still had an extended trend, wherein thifensulfuron was the most widely used one among the sulfonylurea herbicides. With long residual life of the sulfonylurea herbicides and serious damage of its accumulation in soil to the crop in next cycle, it was found now that the residues of the sulfonylurea herbicides will cause damage to many important crops such as rice, soybean, maize, rape, cotton, beet, flax and sunflower.

Sulfonylurea herbicides degrading strains and genes have the following functions in development of technologies for removal of herbicidal residues and control of its injury: (1) the sulfonylurea herbicide-degrading genes could be introduced into the crops by modern biotechnologies to construct the corresponding herbicide-resistant transgenic crops; (2) the sulfonylurea herbicide-degrading strains and genes could be used as microbial or enzyme agents to remove the sulfonylurea herbicide residues in soil. In addition, the sulfonylurea herbicide-degrading genes could be used for biotransformation in synthesis of useful chemical products and drugs. Therefore, the sulfonylurea herbicide-degrading genes are very valuable in theory and application for removal of herbicide damage and in biotransformation field.

Thifensulfuron, a sulfonylurea herbicide, which is increasingly and widely used, persists for a long time in soil and the residues consistently injure subsequent rotation crops Development of herbicide-resistant transgenic crops is a good way to prevent crops from herbicide injury. However, up to now, no report about genes enabling the degradation of thifensulfuron has been reported.

SUMMARY OF THE INVENTION

The present invention provides a thifensulfuron hydrolase gene used for construction of thifensulfuron-resistant transgenic crops, removal of thifensulfuron and haloxyfop-R-methyl from soil and water, and biotransformation in drug synthesis.

Another object of the present invention is to provide the uses of the gene.

The present invention is achieved by the following methods:

A thifensulfuron hydrolase gene tsmE, with a nucleotide sequence of SEQ ID NO. 1.

Strain *Methylophilus* sp. S113, capable of degrading a variety of sulfonylurea herbicides, was used in this study. The strain was isolated from sulfonylurea herbicide-contaminated soil and deposited in the China General Microbiological Culture Collection Center (CGMCC), with accession number CGMCC 1479, dated Oct. 12, 2005. The results of mass spectrography analysis indicated that the crude enzyme of strain S113 could hydrolyze thifensulfuron to thiophenesulfonic acid.

Figure 1:
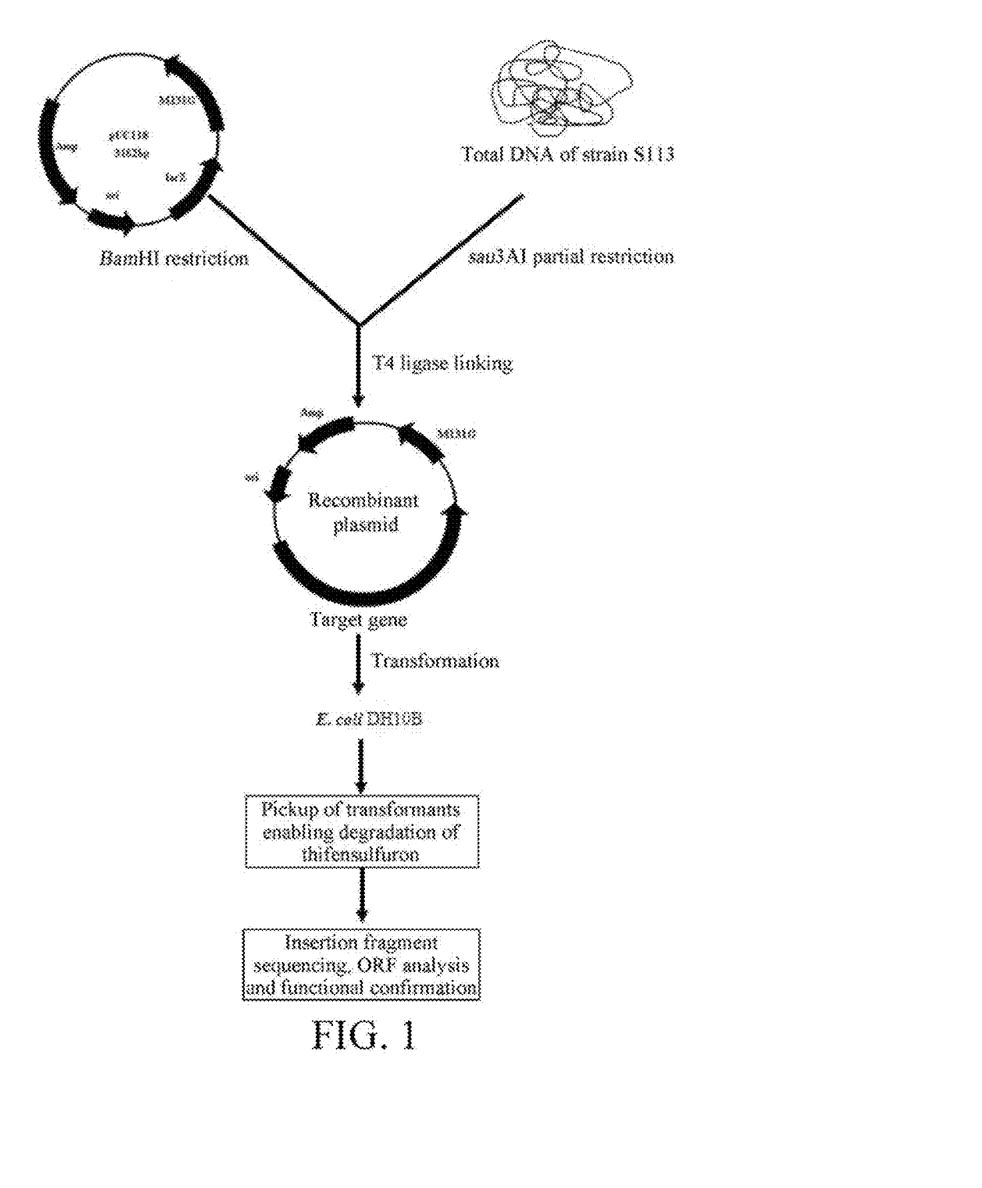
FIG. 1 is a scheme for cloning of the thifensulfuron hydrolase gene tsmE.
Figure 2:
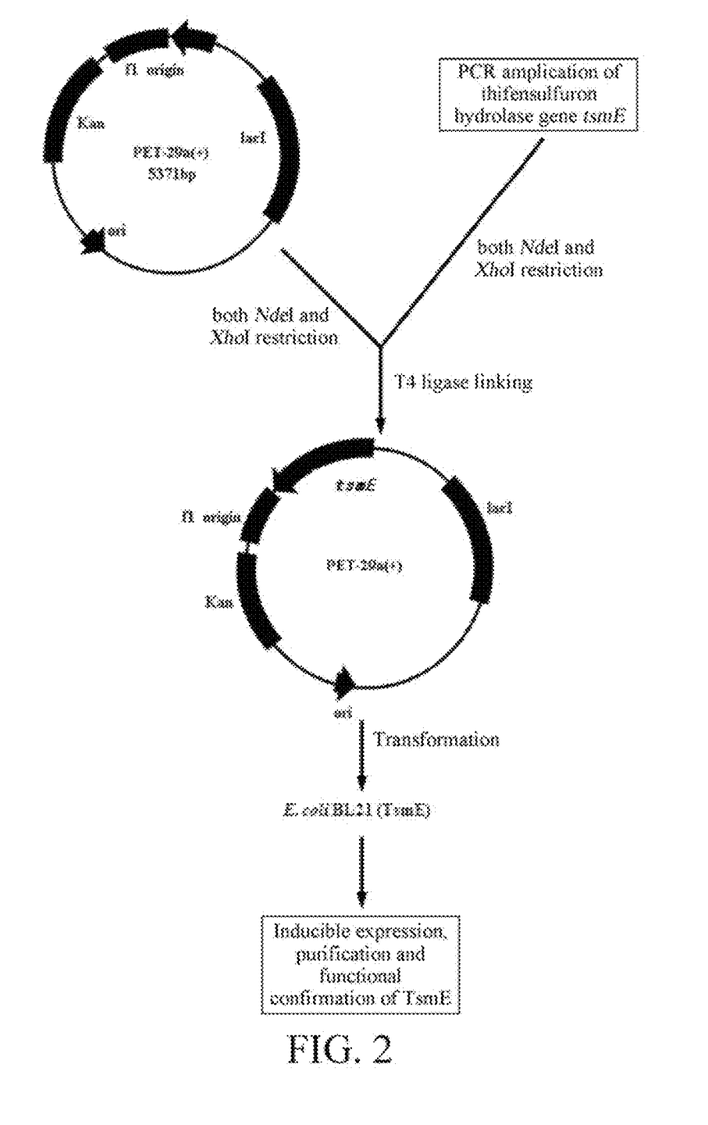
FIG. 2 is a scheme for expression of TsmE in BL21 (pET-29a (+)).

The thifensulfuron hydrolase gene was cloned by shotgun method (see FIG. 1).

A strategy used for cloning of the thifensulfuron hydrolase gene is a shotgun method (see FIG. 1). Initially, total DNA was extracted from strain S113, and partially digested with Sau3AI. The fractions containing approximately 4- to 6-kb DNA fragments were pooled, ligated into the BamHI site of the cloning plasmid pUC118, and transformed into *E. coli* DH10B(ilvG$^+$)-competent cells for construction of total DNA library of the strain S113. The library was spread on MSM (minimum salt medium) plates containing 5 g/L glucose, 100 mg/L ampicillin, 200 mg/L valine, 200 mg/L leucine, and 10 mg/L thifensulfuron and incubated at 37° C. for 24 h. Transformant, which was introduced with a thifensulfuron de-esterification gene, could grow in the above medium due to the ability to convert thifensulfuron to thiophenesulfonic acid, which was inactive and could not inhibit *E. coli*. The visible colonies were picked, purified, and tested for the ability to degrade thifensulfuron using HPLC analysis.

Using *E. coli* DH10B (ilvG$^+$) as the recipient strain for library construction, one transformant that was able to develop a visible colony on the plate was obtained. The results of degradation experiments suggested that the insert fragment of the transformant contains the sulfonylurea herbicide deesterification esterase gene. The sequencing result showed that the inserted fragment in the transformant was 5,143 bp long; 18 complete open reading frames (ORFs) (more than 150 bp) were identified by computer analysis. According to the results of the Blastp program, one ORF shared similarities with some putative or hypothetical esterases (highest identity, 37%). The ORF was subcloned to the linearized vector pMD18-T and transformed into *E. coli* DH10B. The resting cells of the subclone showed the ability to degrade thifensulfuron. Therefore, we concluded that this ORF was the target gene encoding the sulfonylurea herbicide deesterification esterase and designated as tsmE.

The amino acid sequence of the thifensulfuron hydrolase protein TsmE was showed in SEQ ID NO. 2.

A recombinant expression vector containing the thifensulfuron hydrolase gene tsmE.

A recombinant expression vector was obtained by insertion of the thifensulfuron hydrolase gene tsmE into the NdeI and HindIII sites of pET-29a (+).

A genetically engineered microorganism comprising the thifensulfuron hydrolase gene tsmE.

For the genetically engineered bacterium, *E. coli* BL21 (DE3) is preferred as the recipient strain.

A use of the thifensulfuron hydrolase gene tsmE in construction of the thifensulfuron-resistant transgenic crops.

A use of the thifensulfuron hydrolase gene tsmE in degradation of thifensulfuron and haloxyfop-R-methyl.

A use of the thifensulfuron hydrolase protein TsmE in degradation of thifensulfuron and haloxyfop-R-methyl.

A use of the thifensulfuron hydrolase protein TsmE in removal of residues of herbicide thifensulfuron and haloxyfop-R-methyl from soil and water.

The advantageous effects of the present invention are as follows:

1. In the present invention, the thifensulfuron hydrolase gene tsmE was cloned from strain S113 (CGMCC 1479) by the shotgun method. The results of a Blastp search in the NCBI revealed that tsmE is a new gene with full length (from start codon to terminal codon) of 1194 bp, G+C content of 51.09%, encoding 398 amino acids.

Figure 4:
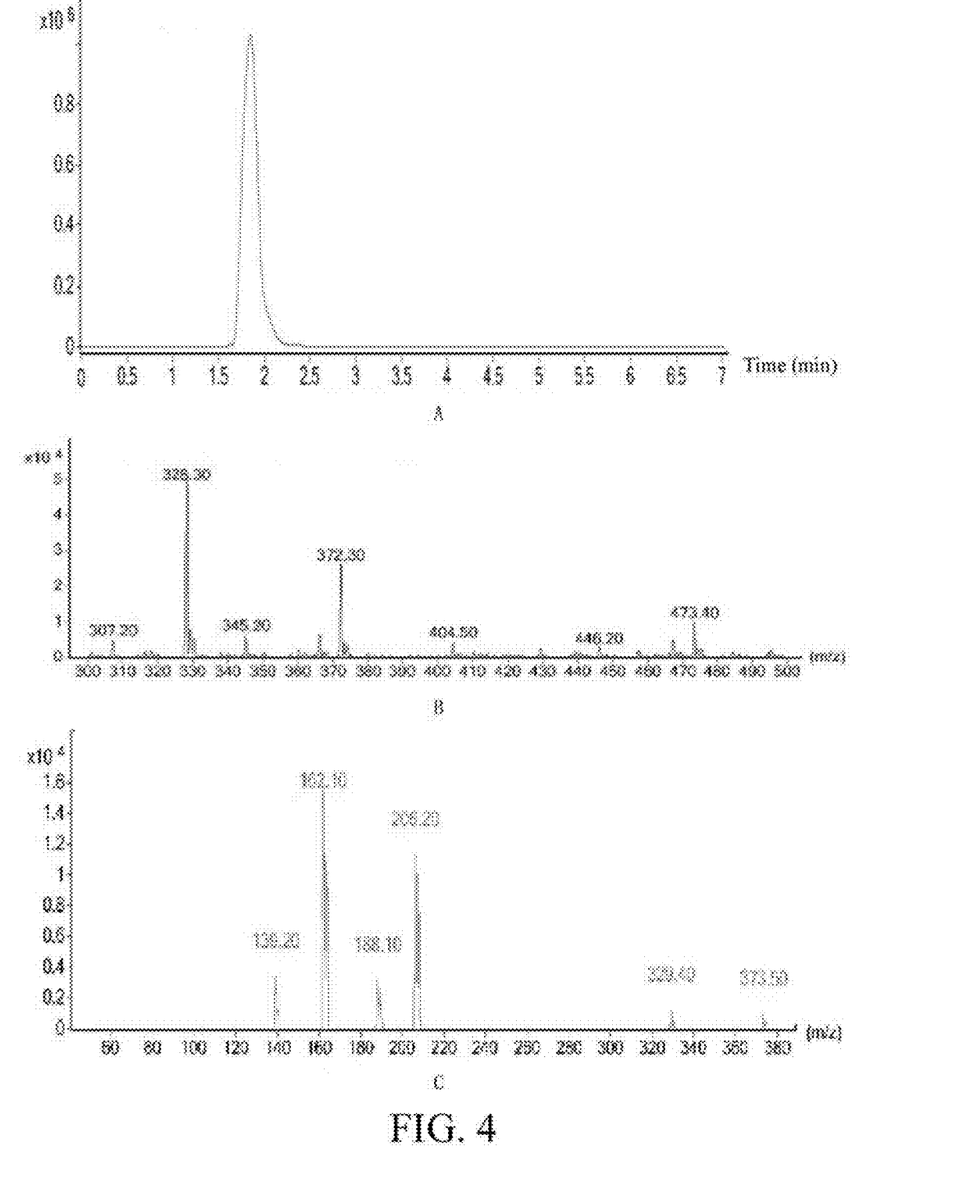
FIG. 4 is a graph of the LC-MS profile of the metabolite produced during degradation of thifensulfuron by the hydrolase TsmE.
Figure 5:
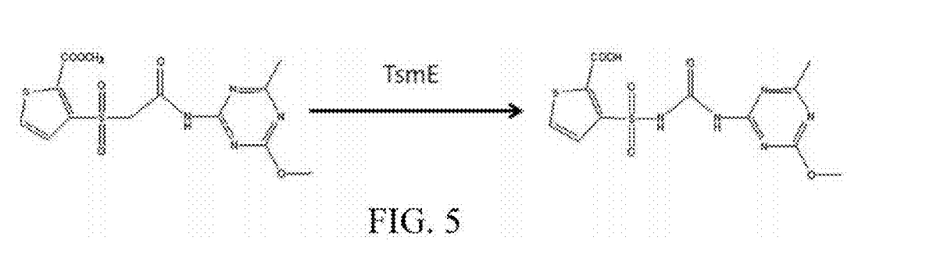
FIG. 5 is a degradation pathway of thifensulfuron by TsmE.
Figure 6:
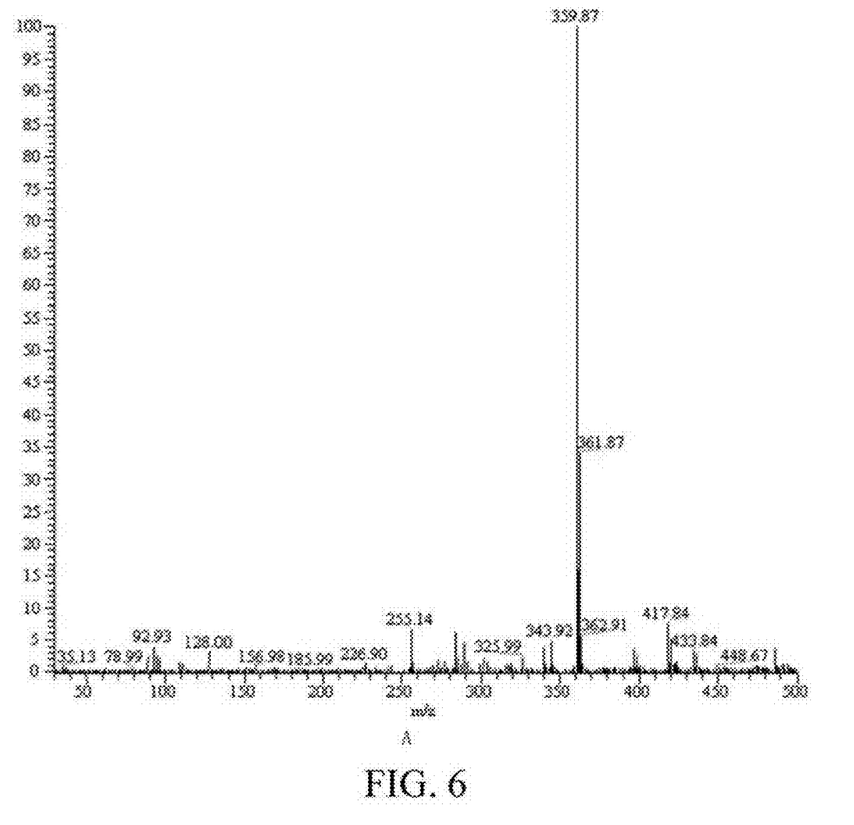
FIG. 6 is an MS/MS profile of haloxyfop-R-methyl degradation by TsmE.
Figure 7:
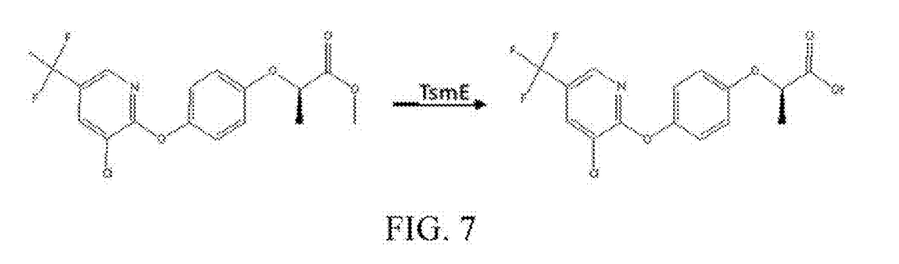
FIG. 7 is a pathway of haloxyfop-R-methyl degradation by TsmE.

2. The thifensulfuron hydrolase TsmE provided by the present invention could degrade completely 100 mg/L thifensulfuron to the corresponding herbicidally inactive thiophenesulfonic acid within 1 hour (see FIG. 4 and FIG. 5). TsmE could also degrade degrade 100 mg/L haloxyfop-R-methyl within 1 hour (see FIG. 6 and FIG. 7). tsmE could be used for construction of the thifensulfuron-resistant transgenic crop, removal of residues of thifensulfuron and haloxyfop-R-methyl from soil and water, and biotransformation in drug synthesis.

BRIEF DESCRIPTION OF THE DRAWINGS

Wherein the lane 1 is protein marker, and the lane 2 is the purified TsmE.

A: a liquid chromatogram for degradation of thifensulfuron by TsmE.

B: a first-order mass spectra for degradation of thifensulfuron by the hydrolase TsmE.

C: a second-order mass spectra for degradation of thifensulfuron by TsmE.

A: a first-order mass spectra for degradation of haloxyfop-R-methyl by TsmE.

B: a second-order mass spectra for degradation of haloxyfop-R-methyl by TsmE.

DETAILED DESCRIPTION OF THE INVENTION

Embodiment 1

Cloning of the Thifensulfuron Hydrolase Gene 1.1 Extraction of Total DNA from Bacterial Genome Cells of strain S113, cultured in R2A medium for 48 h, were harvested by centrifugation and then the total DNA was extracted by the CTAB method as described by F. Osbourne et al, ed. Concise Guide to molecular biology experiments. The total DNA was dissolved in TE buffer (pH8.0), and stocked at −20° C.

1.2 Digestion of the Total DNA of Strain S113

The total DNA of strain S113 was partial digested by Sau3AI 1.3 DNA Recovery

The restricted total DNA was purified by electrophoresis (TAE buffer), and recovered by a recovering kit (Axygen Biosciences, china). The recovered DNA was dissolved in 10 mmol/L Tris-HCl (pH8.0) and stocked at −20° C.

1.4 Enzymatic Ligation

The reaction system was as follows:

| | |
|---|---|
| pUC118 (BamHI) | 0.1 µg |
| Total DNA fragment | 0.1 µg |
| 10 × ligase buffer | 1 µl |
| T4DNA ligase | 0.5 µl |
| Double distilled water | Ad to 10 µl |

Incubation at 16° C. for 12 hours.

1.5 Preparation of the E. coli DH10B-Competent Cells

The E. coli DH10B was commercially available from the Shanghai Invitrogen Biotechnologies Co., Ltd. The AHAS II isozymes gene ilvG of the E. coli DH10B was activated using Red-mediated recombination to create E. coli DH10B (ilvG$^+$). The competent cells of E. coli DH10B(ilvG$^+$) was prepared according to the method described by F. Osbourne et al, ed. Concise Guide to molecular biology experiments. P22-23.

1.6 Transformation

10 µl ligated product was transformed into 200 µl E. coli DH10B(ilvG$^+$)-competent cells according to the method described by F. Osbourne et al, ed. Concise Guide to molecular biology experiments. P23. The library was spread on MSM (minimum salt medium) plates containing 5 g/L glucose, 100 mg/L ampicillin, 200 mg/L valine, 200 mg/L leucine, and 10 mg/L thifensulfuron and incubated at 37° C. for 24 h. The visible colonies were picked, purified, and tested further for the ability to degrade thifensulfuron using HPLC analysis. The base salt medium was formulated from 5.0 glucose, 1.0 $NH_4NO_3$, 1.0 NaCl, 1.5 $K_2HPO_4$, 0.5 $KH_2PO_4$, and 0.2 $MgSO_4.7H_2O$ pH 7.0.

1.7 Gene Nucleotide Sequencing

The inserted fragment in the positive transformant capable of transforming thifensulfuron to thiophenesulfonic acid was sequenced using an automated sequencer (model 3730; Applied Biosystems) by Shanghai Invitrogen Biotechnologies Co., Ltd. The nucleotide sequence of the thifensulfuron hydrolase gene tsmE is presented in SEQ ID NO. 1, and the deduced 398 amino acid sequence was presented in SEQ ID NO. 2.

Embodiment 2

Expression of the Thifensulfuron Hydrolase Gene tsmE in E. coli BL21 (pET-29a (+))

2.1 PCR Amplification of tsmE tsmE was amplified by PCR from genomic DNA of strain S113 (CGMCC 1479) with forward primer: 5'-TGCAGA CATATGGAAACCGATAAAAAAAC-3 (SEQ ID NO. 3) and reverse primer: 5'-TGCAGA GAATTCCCTTCCATAAGAGCGCCGAT-3' (SEQ ID NO. 4).

The system for amplification was as follows:

| | |
|---|---|
| Primer star DNA Polymerase (5 U/μl) | 0.5 μl |
| 5 × PCR Buffer II (Mg$^{2+}$Plus) | 10 μl |
| dNTP Mixture (each 2.5 mM) | 5 μl |
| Template DNA | 10 ng |
| Forward primer (20 μM) | 1 μl |
| Reverse primer (20 μM) | 1 μl |
| Sterilized distilled water | Ad to 50 μl |

PCR amplification procedure was as follows:
a. denaturation at 95° C. for 3 min;
b. denaturation at 95° C. for 1.5 min, annealing at 53° C. for 0.5 min, Extension at 72° C. for 1.5 min, for 25 cycles;
c. Terminal extension at 72° C. for 10 min.

2.2 Digestion of PCR Products with NdeI and HindIII
The system for digestion was as follows:

| | |
|---|---|
| NdeI | 1 μl |
| HindIII | 1 μl |
| DNA | ≤1 μg |
| Sterilized distilled water | Ad to 20 μl |

Reaction was carried out for about 3 hours in a water bath at 37° C. The digested product was recovered from gel after running on 2% agarose gel electrophoresis.

2.3 Digestion of pET-29a(+) with NdeI and HindIII (with Reference to 2.2).

2.4 Transformation

The recovered fragment in 2.2 was linked to the NdeI and HindIII-digested pET-29a (+) in 2.3 (with reference to 1.5). The linked pET-29a (+) recombinant plasmid containing the tsmE was transformed into the host bacteria *E. coli* BL21 (DE3) to generate the recombinant microorganism BL21 (TsmE).

2.5 Functional Expression and Purification of TsmE

Figure 3:
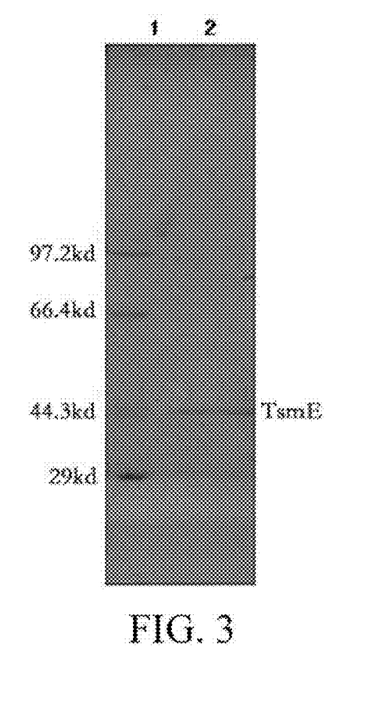
FIG. 3 is an electropherogram of the SDS-PAGE analysis of the purified TsmE.

*E. coli* BL21 (TsmE) was cultured in the LB culture medium until OD600 nm was reached 0.6 to 0.8; 1 mM IPTG was added to the culture for induction, and the culture was incubate for another 4 hours at 30° C. 100 ml culture was centrifuged, and the cell was re-suspended in 10 ml PBS buffer (50 mM, pH 7.0), ultrasonicated (Auto Science, UH-650B ultrasonic processor, 30% intensity) for 5 minutes, and then centrifuged. The supernatant was collected and the recombinant TsmE was purified to homogeneity using Ni-nitrilotriacetic acid affinity chromatography (FIG. 3).

2.6 Enzyme Assay.

The enzymatic activities towards thifensulfuron and haloxyfop-R-methyl were assayed in 1 ml of 50 mM potassium phosphate buffer (pH 7.0) at 30° C. for 20 min. The reactions were initiated by the addition of 50 μl purified TsmE to the final concentration of 0.2 mM thifensulfuron or 0.2 mM haloxyfop-R-methyl. Reactions were stopped by adding 3 ml dichloromethane and cooling in liquid nitrogen. The organic phase was dried over anhydrous sodium sulfate, and then the concentration of thifensulfuron and haloxyfop-R-methyl were determined by reverse HPLC. One unit of enzyme activity was defined as the amount of enzyme that converted 1 μM of thifensulfuron or haloxyfop-R-methyl to its parent acid form. The results of degradation test showed that the purified TsmE degrade completely 100 mg/L thifensulfuron or haloxyfop-R-methyl within 1 hour, and the specific enzyme activities of TsmE to thifensulfuron and haloxyfop-R-methyl were 67 U/mg and 55 U/mg protein, respectively.

2.7 Identification of the Metabolites 2.7.1 Identification of Metabolites of Thifensulfuron The supernatants of the enzyme reaction were filtered through a 0.2 μm-pore-size filter and analyzed by LC-MS with the liquid chromatography conditions: chromatographic column: Agilent Zorbax XDB-C18 column (2.1×50 mm, 3.5 μm), mobile phase: methanol:water=80:20, flow rate: 0.25 ml/min, and UV detection wavelength: 255 nm. The first-order MS conditions: ion detection mode: multi-reaction ion detection; ion polar: negative ion; ionization mode: electro-spray ionization; capillary voltage: 4000 volts; drying gas temperature: 330° C.; flow rate of drying gas: 10.0 L/min; atomized gas pressure: 35 psi; collision voltage: 135 volts; mass scanning range (m/z): 300-500. The second-order ion MS conditions: collision voltage: 90 volts; mass scanning range (m/z): 30-400.

The results of the LC-MS spectrogram (see FIG. 4A) showed that the metabolite of thifensulfuron has a retention time of 1.95 min. In the first-order mass spectrogram (see FIG. 4B), there was a negative ion peak of its molecule with m/z 372.30; and in the second-order mass spectrogram (see FIG. 4C, there were the fragments with m/z 162.10, 188.10 and 206.20, consistent with thiophenesulfonic acid. Therefore, TsmE catalyzed the de-esterification of thifensulfuron that gave rise to thiophenesulfonic acid. (see FIG. 5).

2.7.2 Identification of Metabolites from Degradation of Haloxyfop-R-Methyl

The metabolite of haloxyfop-R-methyl was determined by tandem mass spectroscopy. 2 ml supernatants of the enzyme reaction was extracted and blew to dryness and dissolved in 100 μL methanol. The metabolite was analysed with tandem mass spectroscopy at the following conditions: MS/MS (Finnigan TSQ Quantum Ultra AM, Thermal, U.S.A.), electro-spray ionization, detection with both positive and negative ion, and mass scanning range (m/z): 30-1200.

In the first-order MS/MS mass spectrogram (see FIG. 6A), there was a negative ion peak with m/z 359.87; and in the second-order mass spectrogram (see FIG. 6B), there was a fragment with m/z 287.60, consistent with the metabolite 2-[4-(3-chloro-5-trifluoromethyl-2-pyridyloxy)phenoxy]propanoic acid. Therefore, TsmE catalyzed the hydrolysis of haloxyfop-R-methyl to 2-[4-(3-chloro-5-trifluoromethyl-2-pyridyloxy)phenoxy]propanoic acid (see FIG. 7).

The microorganisms used in the embodiments were available from:

| | |
|---|---|
| pUC118 (BamHI) | TAKARA BIOTECHNOLOGY (DALIAN) CO., LTD. |
| *E. coli* DH10B | Shanghai Invitrogen Biotechnologies Co., Ltd. |
| *E. coli* expression vector pET-29a(+) | Novegen Co. |
| Host *E. coli* BL21 (DE3) for expression | Shanghai Invitrogen Biotechnologies Co., Ltd. |

Deposit Information of the Strain

Strain *Methylophilus* sp. S113 was deposited in the China General Microbiological Culture Collection Center (CGMCC), Institute of Microbiology, Chinese Academy of Sciences. NO. 1 Beichen West Road, Chaoyang District, Beijing 100101. China, with accession number CGMCC 1479, dated Oct. 12, 2005.

What is claimed is:

1. A transgenic bacterium comprising a vector, wherein said vector comprises a nucleotide sequence encoding a thifensulfuron hydrolase gene tsmE, and wherein said nucleotide sequence comprises SEQ ID NO. 1.

2. A transgenic bacterium comprising a vector wherein said vector comprises a thifensulfuron hydrolase gene tsmE comprising the nucleotide sequence of SEQ ID NO. 1, and wherein the tsmE gene encodes a thifensulfuron hydrolase protein TsmE comprising the amino acid sequence of SEQ ID NO. 2.

3. A transgenic bacterium comprising a pET plasmid comprising a thifensulfuron hydrolase gene tsmE comprising the nucleotide sequence of SEQ ID NO. 1 which encodes a thifensulfuron hydrolase protein TsmE comprising the amino acid sequence of SEQ ID NO. 2.

4. A recombinant expression vector, wherein said vector comprises:
   (i) a heterologous regulatory element; and
   (ii) a thifensulfuron hydrolase gene tsmE comprising the nucleotide sequence of SEQ ID NO. 1 and encoding a thifensulfuron hydrolase protein TsmE comprising the amino acid sequence of SEQ ID NO. 2.

5. A method of removing residues of thifensulfuron and haloxyfop-R-methyl from soil or water comprising the steps of:
   preparing a recombinant expression vector according to claim 4;
   transforming a soil bacterium with the vector; and
   introducing the transformed bacterium to the soil or water.

6. A method of degrading thifensulfuron comprising the steps:
   preparing the transgenic bacterium as in claim 3;
   purifying the produced TsmE from said bacterium; and
   adding the TsmE to thifensulfuron, whereby the TsmE degrades thifensulfuron to thiophenesulfonic acid.

7. A method of degrading haloxyfop-R-methyl comprising the steps:
   preparing the transgenic bacterium as in claim 3;
   purifying the produced TsmE from said bacterium; and
   adding the TsmE to haloxyfop-R-methyl, whereby the TsmE degrades haloxyfop-R-methyl to propanoic acid.

* * * * *